(12) United States Patent
Tsuzuki et al.

(10) Patent No.: US 8,877,444 B2
(45) Date of Patent: Nov. 4, 2014

(54) **MARKER FOR IDENTIFYING VARIETY/LINE OF PLANT OF THE GENUS *SACCHARUM* AND THE USE THEREOF**

(75) Inventors: Shoko Tsuzuki, Nagoya (JP); Hiroyuki Enoki, Anjou (JP); Satoru Nishimura, Nagoya (JP); Naoko Tsurumaru, Nagoya (JP)

(73) Assignee: Toyota Jidosha Kabushiki Kaisha, Aichi-ken (JP)

( * ) Notice: Subject to any disclaimer, the term of this patent is extended or adjusted under 35 U.S.C. 154(b) by 188 days.

(21) Appl. No.: 13/378,295

(22) PCT Filed: Jul. 7, 2010

(86) PCT No.: PCT/JP2010/004425
§ 371 (c)(1),
(2), (4) Date: Dec. 14, 2011

(87) PCT Pub. No.: WO2011/004594
PCT Pub. Date: Jan. 13, 2011

(65) Prior Publication Data
US 2012/0094302 A1    Apr. 19, 2012

(30) Foreign Application Priority Data

Jul. 7, 2009   (JP) ................................. 2009-160620

(51) Int. Cl.
*C12Q 1/68*   (2006.01)
*C12P 19/34*  (2006.01)

(52) U.S. Cl.
CPC ........ *C12Q 1/6895* (2013.01); *C12Q 2600/156* (2013.01)
USPC ....................................... 435/6.12; 435/91.2

(58) Field of Classification Search
USPC .............................................. 435/6.12, 91.2
See application file for complete search history.

(56) References Cited

U.S. PATENT DOCUMENTS

2010/0021916 A1*  1/2010  Matsuoka et al. ................ 435/6

FOREIGN PATENT DOCUMENTS

WO   WO 2008/083456 A1   7/2008

OTHER PUBLICATIONS

Edited by Japanese Society for Tropical Agriculture, Tropical Agriculture, Oct. 15, 2004, vol. 48, Extra Issue 2, pp. 61-62.
Edited by Japanese Society for Tropical Agriculture, Tropical Agriculture, Mar. 27, 2004, vol. 48, Extra Issue 1, pp. 107-108.
A. Selvi, et al., "Evaluation of maize microsatellite markers for genetic diversity analysis and fingerprinting in sugarcane", Genome, Jun. 2003, pp. 394-403, vol. 46, No. 3, XP-002601265.
L. R. Pinto, et al., "Characterization of novel sugarcane expressed sequence tag microsatellites and their comparison with genomic SSRs", Plant Breeding, Aug. 2006, pp. 378-384, vol. 125, No. 4, XP-002601263.
Swarup K. Parida, et al., "Informative genomic microsatellite markers for efficient genotyping applications in sugarcane", Theoretical and Applied Genetics, Jan. 2009, pp. 327-338, vol. 118, No. 2, XP-002601262.
W. Maccheroni, et al., "Development of a dependable microsatellite-based fingerprinting system for sugarcane", Sugar Cane International, Mar. 2009, pp. 47-52, vol. 27, No. 2, XP008127071.
Y. B. Pan, et al., "Molecular Genotyping of Sugarcane Clones with Microsatellite DNA Markers", Maydica, 2003, pp. 319-329, vol. 48.
Yong-Bao Pan, "Highly Polymorphic Microsatellite DNA Markers for Sugarcane Germplasm Evaluation and Variety Identity Testing", Sugar Tech, 2006, pp. 246-256, vol. 8, No. 4, XP-002601264.
International Search Report for PCT/JP2010/004425 dated Dec. 15, 2010.

* cited by examiner

*Primary Examiner* — Kenneth R. Horlick
*Assistant Examiner* — Joyce Tung
(74) *Attorney, Agent, or Firm* — Sughrue Mion, PLLC

(57) ABSTRACT

It is an object of the present invention to provide a method for identifying the variety/line of a plant of the genus *Saccharum* with the use of novel DNA markers that allow high-precision identification of a wide range of varieties/lines of plants of the genus *Saccharum*. A method for identifying the variety/line of a plant of the genus *Saccharum*, comprising using a simple sequence repeat polymorphism in at least one DNA sequence selected from SEQ ID NOS: 1 to 12 is provided.

4 Claims, 5 Drawing Sheets

SEQUENCE LISTING

```
<160> NUMBER OF SEQ ID NOS: 42

<210> SEQ ID NO 1
<211> LENGTH: 253
<212> TYPE: DNA
<213> ORGANISM: Saccharum officinarum

<400> SEQUENCE: 1
ctcacgaaac gatcaagaga tgtacgtcct gaatcctctc ccatcctcca aaaggaaaat      60
catttctctc tctctctctc tctctctctc tctctctctc tctcatcaaa agtaaacaag     120
agaattctat tcgtggccta cacaaaaccc ttccttttct atctcccacg gaaagaatgg     180 tttttcctc aaaggaaaaa aaagggaaaa gataaatatt ttctcctgac gcacaaataa      240
agccatgtag tag                                                         253

<210> SEQ ID NO 2
<211> LENGTH: 335
<212> TYPE: DNA
<213> ORGANISM: Saccharum officinarum

<400> SEQUENCE: 2
acatcaaaac tctcaatcga ttaaaatata gatcatgaac aatgtaacta gaaaaatacc      60
```

```
tgctcagtca tctgttgata cattccagga cctatttgtc gatggtaaac ttcgttcctg      120
cagttgcagc gcctcttcc tggtgctggc tttatgacgt ttttctctct ccaaacctat       180
gacacattga aaattgaaaa gtaaataaca acaacaacaa caacaacaac aacaacaaca      240
acaacaacat agccttttgt cccaagcaag ttggggtagg ctagagatga aaagtaaata      300
caaatactat acttttccct tgtgatcaac acagt                                 335

<210> SEQ ID NO 3
<211> LENGTH: 305
<212> TYPE: DNA
<213> ORGANISM: Saccharum officinarum

<400> SEQUENCE: 3
cctagcaaca taagagggct tatctatctc ttcttcttct tcttcttctt cttcttcttc      60
ttcttcttct tcttcttcgc ttatgtccaa aacttgtggt agaaacttag agggactccg      120
ttgtgttcat gttggtttgg ggggctggag tccactctac accccctaaa tccgcctctc      180
attgtaggca aagttataca cctaccccaa acaagtgact ccatgttgct tctattaaga      240
tttgaattta ctataaacgt aatgacatca taaaaaaagg atcgagctaa aatgtaattc      300
gaatg                                                                  305

<210> SEQ ID NO 4
<211> LENGTH: 505
<212> TYPE: DNA
<213> ORGANISM: Saccharum officinarum

<400> SEQUENCE: 4
actatcgtca agattcctta aatctcctcc atacatgaga ggtgatttag ccattgacca      60
aagtgccatc tgtaaggtca tgtcaaagaa aaaagagttc attactacag aaaaatagat      120
acaacaacaa caacaacaac aacaacaaca acatagcctt ttgtcccaag caagttgggg      180
taggctacag aaaaaataga tacagaacac ttaaatttga agtgatcacc aacaacaacc      240
tgtgctttct gttcatcaag agtaaggtta catttcctgt gaggaccctg atttacacct      300
gcattaacag aagaaaaagg gtctgttttct gatacagctg catgtatatt atttcattca      360
agatattctt ggaaaaagaa taagggaagg gaatggttat gaatttttac gtgttataag      420
taatttatcg cggatagata tttactctat gtgtgtgctt tactcgatct gatctgaata      480
tcaacagaac agactaaaat taagt                                            505

<210> SEQ ID NO 5
<211> LENGTH: 255
<212> TYPE: DNA
<213> ORGANISM: Saccharum officinarum

<400> SEQUENCE: 5
cccttagcct ctaggtgaag tgatgaagcg tgaagttgat gctggtagca acagttcttt      60
tcttcttctt cttcttcttc ttcttcttct tcttcttctt cttcttcttc ttcttcttct      120
tcttcttctt cttcttcttc ttcttctcct cctctttttga ccaacctacg gcaagcaatc     180
gccgggttaa tatccgtaga atgtgtttac gtgcatgttt tagccaatat tcaatctgtc      240
tgttccttct cttgt                                                       255

<210> SEQ ID NO 6
<211> LENGTH: 163
<212> TYPE: DNA
<213> ORGANISM: Saccharum officinarum
```

<400> SEQUENCE: 6

```
ctacccattt tgctgccatc atcccttct tattctcatg ctatatctct tccattcagg    60
ttcctaacga cgagagtgtc taattcgaaa aagaattat atccatcctc cagaaatcct   120
cctcccacca ccaccaccac ccagtctgtt tttagcctgc tag                    163
```

<210> SEQ ID NO 7
<211> LENGTH: 154
<212> TYPE: DNA
<213> ORGANISM: Saccharum officinarum

<400> SEQUENCE: 7

```
acctgtctat attgatccct ggaaaaacct tccgctctct ctcttactct ctttctccct    60
ctctggattt gtgaactacc actgtttata ccaaataaac aagaacttac cgactgatct   120
acacctagaa cggtcctaag gatctaacat tggt                               154
```

<210> SEQ ID NO 8
<211> LENGTH: 276
<212> TYPE: DNA
<213> ORGANISM: Saccharum officinarum

<400> SEQUENCE: 8

```
acacaaccat ccctagatta tactccaacc cctcatcttc agactctacc tccccattgc    60
cctcctcctc ttcctcatct tcatcatcac tttcatccct ttcttgttcc tcctcatcct   120
cgtcgctctc atcaccacca ccacctccag aagaagacaa agactatgaa gtcaaactcg   180
aggatggtgg caaagatgaa ggctcatgat gacatttcta tgaggttgac tgatggctta   240
ttggagcatt taaggcattc ttgaacctcc tcttgt                             276
```

<210> SEQ ID NO 9
<211> LENGTH: 238
<212> TYPE: DNA
<213> ORGANISM: Saccharum officinarum

<400> SEQUENCE: 9

```
ccaccttttt tgttttctc tttcttcttt tccccatttc accttttttac cacaaatgta    60
acccgagccc tccccatgga aactataaaa ggggaggcag ggtccacatc taggacaaga   120
cataaagacg cataagattt cacaatgacc aatcgaaaca cacacctcac acacaaatcc   180
cctgaagaga cctgggatcc gcaccctctc tcgaaagctt gtaaccccta ctatgagt     238
```

<210> SEQ ID NO 10
<211> LENGTH: 121
<212> TYPE: DNA
<213> ORGANISM: Saccharum officinarum

<400> SEQUENCE: 10

```
acggacccga ctaacctgtg ctgttagtgt tgtgtgtgtg tgtgtgtgtg tatatatata    60
tatatatata taccttgcc aggagaagag gattattgta acatctgatc ccatcccatg   120
g                                                                   121
```

<210> SEQ ID NO 11
<211> LENGTH: 145
<212> TYPE: DNA
<213> ORGANISM: Saccharum officinarum

<400> SEQUENCE: 11

```
acatcattgg acgctgttac cttgtgtgtg tgtgtgtgtg tgtgtgtgtg tgtgtgtgtg    60
tgtgtgtgtg tgtgtgtgtg aacaaaggca gtgtgtgttt tcttgcagtt ccagtcttgt   120
atgtctgact gcaatttatt ttcgg                                         145

<210> SEQ ID NO 12
<211> LENGTH: 205
<212> TYPE: DNA
<213> ORGANISM: Saccharum officinarum

<400> SEQUENCE: 12
acaagcctac tcccatactc catagacacc ctctctctct ctagatctct ctctctctct    60
ctctctctct ctctctctct ctctctctct cccaaccctc ttcaactttg tgcatttcct   120
tccctagttg ggacacctaa ttctgacatt ctctcgttca agtgagaatc tacctaggtg   180
aagcaccttc tatgagctcg tctgt                                         205

<210> SEQ ID NO 13
<211> LENGTH: 255
<212> TYPE: DNA
<213> ORGANISM: Saccharum officinarum

<400> SEQUENCE: 13
actccggaca aggtttatga gtttgataag agccctacta tagcaaacaa actagtttct    60
cttcttcttc ttcttcttct tcttcttctt cttcttcttc ttcttcttcc ttccttcctt   120
ccttctttcc tagccagagc cccacacctc tttgagtgat taccatgata tgggcttgtt   180
tcattaaaaa ctctatccaa aaacctagtg aaaaaaatta aatgattgt tagagaaaag   240 atatatcaca tttat                                                    255

<210> SEQ ID NO 14
<211> LENGTH: 255
<212> TYPE: DNA
<213> ORGANISM: Saccharum officinarum

<400> SEQUENCE: 14
ctgaaatatt gaaatactc ctaaaaattt cttcatagga aacatgacag tggtaataaa    60
acatctcaat gaacagaaca caccttttcta ctgtggtact tgaattgaaa gcacctatcc   120
aattgaatgc aagaaacaat agatttgtca tattcatagt tgcaagacat agataaacag   180
agtgctgaac agccaacatg aatatacgat tgctctccag tctggcagtt ctgaaacaca   240
agccagtttc agaaa                                                    255

<210> SEQ ID NO 15
<211> LENGTH: 20
<212> TYPE: DNA
<213> ORGANISM: Artificial
<220> FEATURE:
<223> OTHER INFORMATION: primer

<400> SEQUENCE: 15
cctgaatcct ctcccatcct                                                20

<210> SEQ ID NO 16
<211> LENGTH: 20
<212> TYPE: DNA
<213> ORGANISM: Artificial
<220> FEATURE:
<223> OTHER INFORMATION: primer

<400> SEQUENCE: 16
```

-continued gaagggtttt gtgtaggcca                                                20

<210> SEQ ID NO 17
<211> LENGTH: 20
<212> TYPE: DNA
<213> ORGANISM: Artificial
<220> FEATURE:
<223> OTHER INFORMATION: primer

<400> SEQUENCE: 17
ggtgctggct ttatgacgtt                                                20

<210> SEQ ID NO 18
<211> LENGTH: 20
<212> TYPE: DNA
<213> ORGANISM: Artificial
<220> FEATURE:
<223> OTHER INFORMATION: primer

<400> SEQUENCE: 18
tgcttgggac aaaaggctat                                                20

<210> SEQ ID NO 19
<211> LENGTH: 21
<212> TYPE: DNA
<213> ORGANISM: Artificial
<220> FEATURE:
<223> OTHER INFORMATION: primer

<400> SEQUENCE: 19
cctagcaaca taagagggct t                                              21

<210> SEQ ID NO 20
<211> LENGTH: 20
<212> TYPE: DNA
<213> ORGANISM: Artificial
<220> FEATURE:
<223> OTHER INFORMATION: primer

<400> SEQUENCE: 20
ccaacatgaa cacaacggag                                                20

<210> SEQ ID NO 21
<211> LENGTH: 20
<212> TYPE: DNA
<213> ORGANISM: Artificial
<220> FEATURE:
<223> OTHER INFORMATION: primer

<400> SEQUENCE: 21
ttgaccaaag tgccatctgt                                                20

<210> SEQ ID NO 22
<211> LENGTH: 20
<212> TYPE: DNA
<213> ORGANISM: Artificial
<220> FEATURE:
<223> OTHER INFORMATION: primer

<400> SEQUENCE: 22
tgtagcctac cccaacttgc                                                20

<210> SEQ ID NO 23
<211> LENGTH: 22
<212> TYPE: DNA

```
<213> ORGANISM: Artificial
<220> FEATURE:
<223> OTHER INFORMATION: primer

<400> SEQUENCE: 23
tccggacaag gtttatgagt tt                                              22

<210> SEQ ID NO 24
<211> LENGTH: 20
<212> TYPE: DNA
<213> ORGANISM: Artificial
<220> FEATURE:
<223> OTHER INFORMATION: primer

<400> SEQUENCE: 24
gggctctggc taggaaagaa                                                 20

<210> SEQ ID NO 25
<211> LENGTH: 20
<212> TYPE: DNA
<213> ORGANISM: Artificial
<220> FEATURE:
<223> OTHER INFORMATION: primer

<400> SEQUENCE: 25
gcgtgaagtt gatgctggta                                                 20

<210> SEQ ID NO 26
<211> LENGTH: 20
<212> TYPE: DNA
<213> ORGANISM: Artificial
<220> FEATURE:
<223> OTHER INFORMATION: primer

<400> SEQUENCE: 26
gccgtaggtt ggtcaaaaga                                                 20

<210> SEQ ID NO 27
<211> LENGTH: 20
<212> TYPE: DNA
<213> ORGANISM: Artificial
<220> FEATURE:
<223> OTHER INFORMATION: primer

<400> SEQUENCE: 27
ctgccatcat ccccttctta                                                 20

<210> SEQ ID NO 28
<211> LENGTH: 21
<212> TYPE: DNA
<213> ORGANISM: Artificial
<220> FEATURE:
<223> OTHER INFORMATION: primer

<400> SEQUENCE: 28
agcaggctaa aaacagactg g                                               21

<210> SEQ ID NO 29
<211> LENGTH: 20
<212> TYPE: DNA
<213> ORGANISM: Artificial
<220> FEATURE:
<223> OTHER INFORMATION: primer

<400> SEQUENCE: 29
tgcttgggac aaaaggctat                                                 20
```

```
<210> SEQ ID NO 30
<211> LENGTH: 20
<212> TYPE: DNA
<213> ORGANISM: Artificial
<220> FEATURE:
<223> OTHER INFORMATION: primer

<400> SEQUENCE: 30
tggaccaaaa cgtcaggaat                                                   20

<210> SEQ ID NO 31
<211> LENGTH: 20
<212> TYPE: DNA
<213> ORGANISM: Artificial
<220> FEATURE:
<223> OTHER INFORMATION: primer

<400> SEQUENCE: 31
ccaacccctc atcttcagac                                                   20

<210> SEQ ID NO 32
<211> LENGTH: 20
<212> TYPE: DNA
<213> ORGANISM: Artificial
<220> FEATURE:
<223> OTHER INFORMATION: primer

<400> SEQUENCE: 32
gacgaggatg aggaggaaca                                                   20

<210> SEQ ID NO 33
<211> LENGTH: 20
<212> TYPE: DNA
<213> ORGANISM: Artificial
<220> FEATURE:
<223> OTHER INFORMATION: primer

<400> SEQUENCE: 33
gggaaacaat ttccgtcaga                                                   20

<210> SEQ ID NO 34
<211> LENGTH: 20
<212> TYPE: DNA
<213> ORGANISM: Artificial
<220> FEATURE:
<223> OTHER INFORMATION: primer

<400> SEQUENCE: 34
tgcttgggac aaaaggctat                                                   20

<210> SEQ ID NO 35
<211> LENGTH: 20
<212> TYPE: DNA
<213> ORGANISM: Artificial
<220> FEATURE:
<223> OTHER INFORMATION: primer

<400> SEQUENCE: 35
ctataaaagg ggaggcaggg                                                   20

<210> SEQ ID NO 36
<211> LENGTH: 20
<212> TYPE: DNA
<213> ORGANISM: Artificial
<220> FEATURE:
```

<223> OTHER INFORMATION: primer

<400> SEQUENCE: 36
ccaggtctct tcagggatt                                          20

<210> SEQ ID NO 37
<211> LENGTH: 20
<212> TYPE: DNA
<213> ORGANISM: Artificial
<220> FEATURE:
<223> OTHER INFORMATION: primer

<400> SEQUENCE: 37
cccgactaac ctgtgctgtt                                         20

<210> SEQ ID NO 38
<211> LENGTH: 20
<212> TYPE: DNA
<213> ORGANISM: Artificial
<220> FEATURE:
<223> OTHER INFORMATION: primer

<400> SEQUENCE: 38
catgggatgg gatcagatgt                                         20

<210> SEQ ID NO 39
<211> LENGTH: 20
<212> TYPE: DNA
<213> ORGANISM: Artificial
<220> FEATURE:
<223> OTHER INFORMATION: primer

<400> SEQUENCE: 39
catcattgga cgctgttacc                                         20

<210> SEQ ID NO 40
<211> LENGTH: 21
<212> TYPE: DNA
<213> ORGANISM: Artificial
<220> FEATURE:
<223> OTHER INFORMATION: primer

<400> SEQUENCE: 40
caagactgga actgcaagaa a                                       21

<210> SEQ ID NO 41
<211> LENGTH: 21
<212> TYPE: DNA
<213> ORGANISM: Artificial
<220> FEATURE:
<223> OTHER INFORMATION: primer

<400> SEQUENCE: 41
caagcctact cccatactcc a                                       21

<210> SEQ ID NO 42
<211> LENGTH: 20
<212> TYPE: DNA
<213> ORGANISM: Artificial
<220> FEATURE:
<223> OTHER INFORMATION: primer

<400> SEQUENCE: 42
tgtcccaact agggaaggaa                                         20

MARKER FOR IDENTIFYING VARIETY/LINE OF PLANT OF THE GENUS *SACCHARUM* AND THE USE THEREOF

CROSS REFERENCE TO RELATED APPLICATIONS

This application is a National Stage of International Application No. PCT/JP2010/004425, filed on Jul. 7, 2010, which claims priority from Japanese Patent Application No. 2009-160620, filed on Jul. 7, 2009, the contents of all of which are incorporated herein by reference in their entirety.

TECHNICAL FIELD

The present invention relates to a characteristic DNA sequence containing an SSR sequence developed from the genome of the genus *Saccharum* and a method for identifying the variety/line of a plant of the genus *Saccharum* with the use of the sequence.

BACKGROUND ART

Sugarcane has been cultivated as a raw material for sugar or for alcoholic drink. In addition, sugarcane has been used in a variety of industrial fields, including the use as a raw material for biofuel. Under such circumstances, there is a need to develop a method for identifying a sugarcane variety/line in a convenient manner in order to breed sugarcane varieties having desirable characteristics (e.g., sugar content, enhanced vegetative capacity, sprouting capacity, disease resistance, insect resistance, and cold resistance).

The following three ways may be used for identification of a plant variety/line: "characteristics comparison" for comparison of characteristics data, "comparison of cultivation" for comparison of plants cultivated under the same conditions, and "DNA assay" for DNA analysis. There are many problems in line identification with the use of characteristics comparison or comparison of cultivation, including reduction of precision due to differences in cultivation conditions, lengthy duration of field research that requires a number of steps, and the like. In particular, since sugarcane plants are much larger than other graminaceous crops such as rice and maize, it has been difficult to conduct line identification based on field research.

Meanwhile, in the case of sugarcane, the development of genetic marker technology has been delayed because of genomic complexity. Although the USDA reported genotyping with the use of SSR markers (Non Patent Literature 1), the precision of genotyping is low because of the small numbers of markers and polymorphisms in each marker. In addition, the above genotyping is available only for American/Australian varieties and therefore cannot be used for line identification of the major varieties cultivated in Japan, Taiwan, India, and other countries and of useful genetic resources.

CITATION LIST

Non Patent Literature

NPL 1: Maydica 48 (2003) 319-329 "Molecular genotyping of sugarcane clones with microsatellite DNA markers"

SUMMARY OF INVENTION

Technical Problem

It is an object of the present invention to provide a method for identifying the variety/line of a plant of the genus *Saccharum* with the use of novel DNA markers that allow high-precision identification of a wide range of varieties/lines of plants of the genus *Saccharum*.

Solution to Problem

As a result of intensive studies in order to achieve the above object, the present inventors have found characteristic DNA sequences from a number of DNA fragments derived from the genome of the genus *Saccharum*, such DNA sequences enabling identification of a wide range of varieties/lines of plants of the genus *Saccharum*. This has led to the completion of the present invention.

Specifically, the present invention encompasses the following features.

(1) A method for identifying the variety/line of a plant of the genus *Saccharum*, comprising using a simple sequence repeat polymorphism in at least one DNA sequence selected from SEQ ID NOS: 1 to 12.

(2) The identification method according to (1), comprising using simple sequence repeats in three types of DNA sequences selected from SEQ ID NOS: 1, 2, and 6.

(3) The identification method according to (1), comprising using simple sequence repeats in three types of DNA sequences selected from SEQ ID NOS: 2, 6, and 12.

(4) The identification method according to (1), comprising using a simple sequence repeat polymorphism in any one of DNA sequences of SEQ ID NOS: 1, 2, 3, 4, 5, 6, 7, 8, 10, and 12, wherein a plant of the genus *Saccharum* to be identified is of the variety NiF8 or Ni9.

(5) The identification method according to (1), comprising using a simple sequence repeat polymorphism in any one of DNA sequences of SEQ ID NOS: 1, 2, 3, 4, 5, 6, 7, 8, 11, and 12, wherein a plant of the genus *Saccharum* to be identified is of the variety F177 or Nco310.

(6) The identification method according to (1), comprising using a simple sequence repeat polymorphism in the DNA sequence represented by SEQ ID NO: 12, wherein a plant of the genus *Saccharum* to be identified is a variety cultivated in Japan.

(7) The identification method according to (1), further comprising using simple sequence repeat polymorphisms in the DNA sequence(s) represented by SEQ ID NO(S): 13 and/or 14.

(8) The method according to any one of (1) to (7), wherein identification is carried out by the steps of:
(a) carrying out PCR amplification using DNA extracted from a sugarcane to be identified as a template and a primer set consisting of a forward and reverse primers that specifically amplify a region containing a simple sequence repeat in the selected DNA sequence(s);
(b) determining the molecular weights of amplified DNA fragments; and
(c) performing genotyping of the region containing a simple sequence repeat based on distribution of molecular weights.

(9) The method according to (8), wherein the determination of the molecular weights of the amplified DNA fragments in step (b) is performed by capillary electrophoresis.

(10) The method according to (8), further comprising comparing the genotype determined with that obtained from a known sugarcane variety/line in step (c).

(11) A kit for conducting the method according to any one of (1) to (10), comprising a primer set consisting of a forward and reverse primers that specifically amplify a region containing a simple sequence repeat in the selected DNA sequence(s).

(12) The kit according to (11), further comprising a correspondence table regarding the genotype of a region containing a simple sequence repeat in the selected DNA sequence(s), obtained from known sugarcane varieties/lines.

Advantageous Effects of Invention

The present invention provides a method for identifying the variety/line of a plant of the genus *Saccharum* with the use of novel DNA markers that allow high-precision identification of a wide range of varieties/lines of plants of the genus *Saccharum*. Identification of a wider range of sugarcane varieties with improved precision can be achieved by using the DNA markers of the present invention, if necessary, in combination. In addition, the reproducibility of the method is high.

In addition, the present invention provides a kit for conducting the method of the present invention.

BRIEF DESCRIPTION OF DRAWINGS

FIG. 3-1 shows partial charts of polymorphism detection results for two sugarcane lines (NiF8 and Ni9) with the use of an SSR marker STY133.

FIG. 3-2 shows partial charts of polymorphism detection results for two sugarcane lines (NCO310 and F177) with the use of an SSR marker STY133.

DESCRIPTION OF EMBODIMENTS

Figure 1:
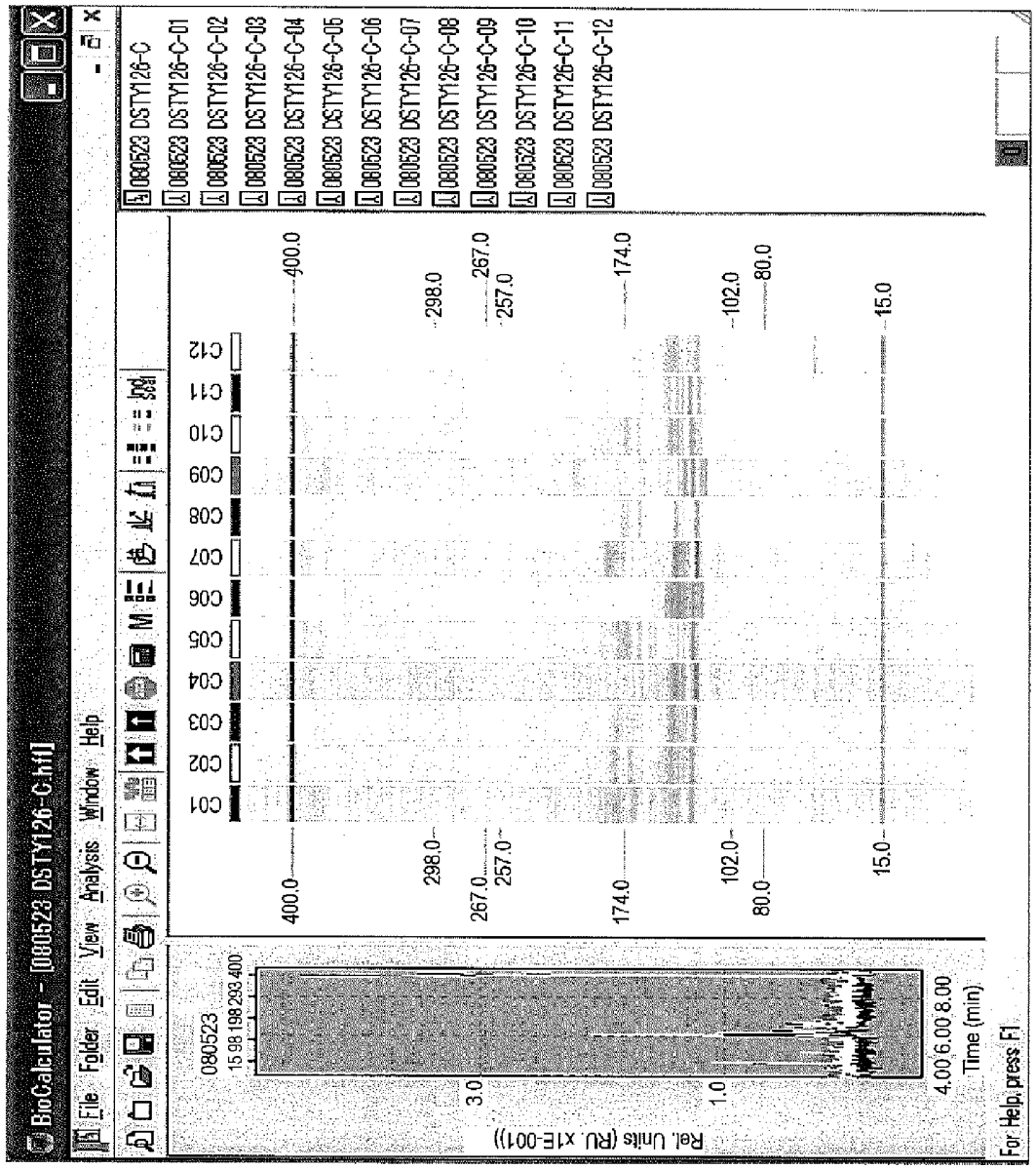
FIG. 1 is a capillary electrophoresis image obtained as a result of PCR amplification of an SSR marker STY126.

Hereinafter, the method for identifying the variety/line of a plant of the genus *Saccharum* of the present invention (hereinafter simply referred to as the method of the present invention) is described.

The term "variety/line" used in the present invention refers to a group of plants that can be distinguished from other groups of plants by all or some of the morphological/ecological characteristics based on their genotype.

According to the present invention, identification of the variety/line of a plant of the genus *Saccharum* is intended to include identification of the variety/line of a plant of the genus *Saccharum* that is unknown in terms of variety/line, and determination of whether or not a plant of the genus *Saccharum* plant that is unknown in terms of the variety/line corresponds to a specific variety/line. For instance, it includes identification as to which variety/line a plant of the genus *Saccharum* that is completely unknown in terms of variety/line corresponds to, determination as to whether or not the plant is a variety cultivated in Japan, and determination as to whether or not a plant of the genus *Saccharum* that is known as a Japanese domestic variety is a main variety in Japan.

According to the present invention, identification of the variety/line of a plant of the genus *Saccharum* further includes determination of the degree of affinity between a plant of the genus *Saccharum* to be tested and a given variety/line.

The method of the present invention is characterized in that a simple sequence repeat (hereinafter also referred to as "SSR") in a characteristic DNA sequence developed from the genome of a plant of the genus *Saccharum* is used. SSR is a repeat of a specific nucleotide sequence having two to several base pairs (bp), which is present in a sporadic pattern in the genomic DNA of an organism. SSR can be represented by $(AC)_n$ or $(GT)_n$ (wherein "A" denotes adenine, "C" denotes cytosine, "G" denotes guanine, "T" denotes thymine, and "n" denotes an integer of 2 or more) depending on the type of nucleotides of which a repeat consists. Differences in the repeat number "n" among varieties/lines form polymorphisms. In general, an SSR can be identified with a highly conserved sequence region adjacent to the SSR. Therefore, each characteristic DNA sequence described herein contains an SSR forming a polymorphism, and sequences adjacent to such SSR.

Characteristic DNA sequences that can be used for the present invention are provided below. Herein, each underlined portion represents an SSR in a characteristic DNA sequence.

```
STY099
                                                               (SEQ ID NO: 1)
ctcacgaaacgatcaagagatgtacgtcctgaatcctctcccatcctccaaaaggaaaatcattTCTCTCTCTCTCTCTCTC TCTCTCTCTCTCTCTCTCTCTCatcaaaagtaaacaagagaattctattcgtggcctacacaaaaccttcctttctatct cccacggaaagaatggttttttcctcaaaggaaaaaaaagggaaaagataaatattttctcctgacgcacaaataaagccat gtagtag STY117
                                                               (SEQ ID NO: 2)
acatcaaaactctcaatcgattaaaatatagatcatgaacaatgtaactagaaaaatacctgacagtcatctgttgataca ttccaggacctatttgtcgatggtaaacttcgttcctgcagttgcagcgcctctttcctggtgctggctttatgacgttttT CTCTCTCcaaacctatgacacattgaaaattgaaaagtaaataaCAACAACAACAACAACAACAACAACAACAACAACAACA Acatagccttttgtcccaagcaagttggggtaggctagagatgaaaagtaaatacaaatactatacttttcccttgtgatca acacagt STY120
                                                               (SEQ ID NO: 3)
cctagcaacataagagggcttatctatcTCTTCTTCTTCTTCTTCTTCTTCTTCTTCTTCTTCTTCTTCTTCTtcgctt
```

-continued atgtccaaaacttgtggtagaaacttagagggactccgttgtgttcatgttggtttgggggctggagtccactctacaccc cctaaatccgcctctcattgtaggcaaagttatacacctaccccaaacaagtgactccatgttgcttctattaagatttgaa tttactataaacgtaatgacatcataaaaaaggatcgagctaaaatgtaattcgaatg

STY123

(SEQ ID NO: 4)

actatcgtcaagattccttaaatctcctccatacatgagaggtgatttagccattgaccaaagtgccatctgtaaggtcatg tcaaagaaaaaagagttcattactacagaaaaatagataCAACAACAACAACAACAACAACAACAACAAcatagccttttgt cccaagcaagttggggtaggctacagaaaaaatagatacagaacacttaaatttgaagtgatcacCAACAACAAcctgtgct ttctgttcatcaagagtaaggttacatttcctgtgaggaccctgatttacacctgcattaacagaagaaaaagggtctgttt ctgatacagctgcatgtatattatttcattcaagatattcttggaaaaagaataagggaagggaatggttatgaatttttac gtgttataagtaatttatcgcggatagatatttactctaTGTGTGTGctttactcgatctgatctgaatatcaacagaacag actaaaattaagt

STYI33

(SEQ ID NO: 5)

CccttagcctctaggtgaagtgatgaagcgtgaagttgatgctggtagcaacagttcttttTCTTCTTCTTCTTCTTCTTCTT CTTCTTCTTCTTCTTCTTCTTCTTCTTCTTCTTCTTCTTCTTCTTCTTCTICTTCTTCTTCTTCTTCTcctcctcttttgaccaa cctacggcaagcaatcgccgggttaatatccgtagaatgtgtttacgtgcatgttttagccaatattcaatctgtctgttcc ttctcttgt

STY137

(SEQ ID NO: 6)

ctacccattttgctgccatcatccccttcttattctcatgctatatctcttccattcaggttcctaacgacgagagtgtcta attcgaaaaaagaattatatccatcctccagaaatcctcctcCCACCACCACCACCAcccagtctgtttttagcctgctag

STY144

(SEQ ID NO: 7)

acctgtctatattgatccctggaaaaaccttccgcTCTCTCTCTttaCTCTCTttctccCTCTCTggatttgtgaactaccac tgtttataccaaataaacaagaacttaccgactgatctacacctagaacggtcctaaggatctaacattggt

STY145

(SEQ ID NO: 8)

acacaaccatccctagattatactccaaccccctcatcttcagactctacctccccattgcCCTCCTCCTcttcctcatctTC ATCATCActttcatccctttcttgttcctcctcatcctcgtcgctctcatcaCCACCACCAcctccAGAAGAAGAcaaagac tatgaagtcaaactcgaggatggtggcaaagatgaaggctcatgatgacatttctatgaggttgactgatggcttattggag catttaaggcattcttgaacctcctcttgt

STY166

(SEQ ID NO: 9)

ccacctttttgttttctctttcttcttttccccatttcacctttttaccacaaatgtaacccgagccctccccatggaaa ctataaaaggggaggcagggtccacatctaggacaagacataaagacgcataagatttcacaatgaccaatcgaaACACACA CctcACACACaaatcccctgaagagacctgggatccgcacccTCTCTCgaaagcttgtaaccctactatgagt

STY168

(SEQ ID NO: 10)

acggacccgactaacctgtgctgttagtgtTGTGTGTGTGTGTGTGTGTATATATATATATATATATATAccttgcag gagaagaggattattgtaacatctgatcccatcccatgg

STY173

(SEQ ID NO: 11)

acatcattggacgctgttacctTGTGTGTGTGTGTGTGTGTGTGTGTGTGTGTGTGTGTGTGTGTGTGTGTGaa caaaggcagTGTGTGttttcttgcagttccagtcttgtatgtctgactgcaattttatttttcgg

STY200

(SEQ ID NO: 12)

acaagcctactcccatactccatagacacccTCTCTCTCTCtagaTCTCTCTCTCTCTCTCTCTCTCTCTCTCTCTCTCT -continued

```
CTCTCTCTCccaaccctcttcaactttgtgcatttccttccctagttgggacacctaattctgacatTCTCTCgttcaagtg agaatctacctaggtgaagcaccttctatgagctcgtctgt
```

In the method of the present invention, the above characteristic DNA sequences can be used alone or in combination depending on a plant of the genus *Saccharum* to be tested.

For instance, if the variety/line of a plant of the genus *Saccharum* to be tested is completely unknown, a wide range of varieties/lines cultivated in Japan and foreign countries can be identified by selecting three different characteristic DNA sequences STY099, STY117, and STY137 and using SSR polymorphisms in these DNA sequences in combination.

If it is highly probable that the variety/line of a plant of the genus *Saccharum* to be tested is a variety cultivated in Japan, the variety/line can be identified by selecting three different varieties that have been introduced into Japan described herein include, but are not limited to, F177, Nco310, and F172.

Persons skilled in the art can clearly understand which characteristic DNA sequence should be selected depending on a plant of the genus *Saccharum* to be tested, with reference to table 4 shown herein below.

Further, in the method of the present invention, either one of or both of the characteristic DNA sequence STY127 and STY162 given below can also be used.

```
STY127
                                                                 (SEQ ID NO: 13)
actccggacaaggtttatgagtttgataagagccctactatagcaaacaaactagtttcTCTTCTTCTTCTTCTTCTTCTTC TTCTTCTTCTTCTTCTTCTTCTTCTtccttccttccttccttctttcctagccagagccccacacctctttgagtgattacc atgatatgggcttgtttcattaaaaactctatccaaaaacctagtgaaaaaaattaaaatgattgttagagaaaagATATAT cacatttat STY162
                                                                 (SEQ ID NO: 14)
ctgaaatattgaaaatactcctaaaaatttcttcataggaaacatgacagtggtaataaaacatctcaatgaacagaACA CACctttctactgtggtacttgaattgaaagcacctatccaattgaatgcaagaaacaatagatttgtcatattcatagt tgcaagacatagataaacagagtgctgaacagccaacatgaatatacgattgctctccagtctggcagttctgaaacaca agccagtttcagaaa
``` characteristic DNA sequences STY117, STY137, and STY200 and using SSR polymorphisms in these DNA sequences in combination.

If it is known that the variety/line of a plant of the genus *Saccharum* to be tested is either NiF8 or Ni9, which are the main varieties in Japan, the variety/line can be identified as NiF8 or Ni9 by selecting one characteristic DNA sequence from the group consisting of STY099, STY117, STY120, STY123, STY133, STY137, STY144, STY145, STY168, and STY200 and using the SSR polymorphism in the DNA sequence.

If it is known that the variety/line of a plant of the genus *Saccharum* to be tested is either F177 or Nco310, which are the main varieties that have been introduced into Japan, the variety/line can be identified as F177 or Nco310 by selecting one characteristic DNA sequence from the group consisting of STY099, STY117, STY120, STY123, STY133, STY137, STY144, STY145, STY173, and STY200 and using the SSR polymorphism in the DNA sequence.

If it is known that the variety/line of a plant of the genus *Saccharum* to be tested is a variety cultivated in Japan, a specific variety/line can be identified by selecting STY200 as the characteristic DNA sequence and using the SSR polymorphism in the DNA sequence.

Examples of varieties cultivated in Japan described herein include, but are not limited to, Ni1, NiN2, NiF3, NiF4, NiF5, Ni6, NiN7, NiF8, Ni9, NiTn10, Ni11, Ni12, Ni14, Ni15, Ni16, Ni17, NiTn19, NiTn20, Ni22, and Ni23. Examples of main varieties in Japan described herein include, but are not limited to, NiF8, Ni9, NiTn10, and Ni15. Examples of main In the method of the present invention, identification of a plant of the genus *Saccharum* with the use of SSR polymorphisms in the above characteristic DNA sequences can be performed by the following steps (a) to (c):
(a) carrying out PCR amplification using DNA extracted from a target sugarcane to be identified as a template and a primer set consisting of a forward and reverse primers that specifically amplify a region containing SSR (hereinafter also referred to as an "SSR marker") in the above selected characteristic DNA sequence;
(b) determining the molecular weights of amplified DNA fragments; and
(c) performing genotyping for the SSR marker based on distribution of molecular weights.

A DNA sample of a plant of the genus *Saccharum* to be tested which is used in the present invention can be obtained by extraction from tissues, such as seeds, leaves, roots, and stems, of the plant. DNA extraction can be carried out in accordance with a method generally known to persons skilled in the art. For instance, tissue of the plant is minced and homogenized in an appropriate buffer, followed by total DNA extraction by a known DNA extraction method such as phenol extraction. A DNA extraction kit used for this purpose may be a commercially available DNA extraction kit. For example, a Plant Genomics DNA Mini kit (BioGene) can be used.

A primer set used in the step (a) can be designed based on sequence information of the above characteristic DNA sequence such that a region containing an SSR that is a target for polymorphism detection is specifically amplified. In addition, if the above characteristic DNA sequence contains several SSRs, a primer set can be designed such that a region containing a single SSR or several SSRs is amplified. The lengths of a forward primer and a reverse primer used in the present invention are not particularly limited as long as a target region can be specifically amplified. For instance, such length can fall within the range of 15 to 50 nucleotides and preferably 17 to 25 nucleotides.

Examples of a set of primers that can specifically amplify SSR marker in the above characteristic DNA sequence are provided in table 5 shown below.

The primer set used in the present invention is preferably labeled at 5'-end for the convenience of subsequent determination of the molecular weights of amplified DNA fragments. Labeling can be carried out by a means known to persons skilled in the art, and including, but are not limited to, FITC, $^{32}$P, alkaline phosphatase, rhodamine, fluorescamine, dansyl, and derivatives thereof.

PCR conditions for step (a) are not limited as long as a target region can specifically be amplified. For example, such conditions can include 20 to 50 cycles of denaturation at 94 degree C. to 95 degree C. for 10 seconds to 1 minute, annealing at 50 degree C. to 65 degree C. for 10 seconds to 1 minute, and elongation at 72 degree C. for 30 seconds to 10 minutes.

DNA fragments subjected to PCR amplification as described above include a plurality of DNA fragments, which are only different from each other in terms of the repeat number of a target SSR due to the fact that a cultivar of sugarcane is an aneupolyploid.

Next, in step (b), the molecular weights of DNA fragments amplified in step (a) are determined. For molecular weight determination, techniques known to persons skilled in the art such as electrophoresis, mass spectrometry, and sequencing can be used, but are not limited thereto. In the method of the present invention, electrophoresis is preferably used.

Examples of electrophoresis include agarose gel electrophoresis, denatured or non-denatured acrylamide gel electrophoresis, capillary electrophoresis, and the like. As described above, in the present invention, target DNA fragments for molecular weight determination include a plurality of DNA fragments having different molecular weights only in terms of the repeat numbers of an SSR. Therefore, for instance, it is necessary to accurately detect a minute molecular weight difference derived from a very short nucleotide sequence difference of 2 nucleotides. Hence, in the method of the present invention, it is preferable to use high-resolution polyacrylamide gel electrophoresis or capillary electrophoresis, and it is particularly preferable to use capillary electrophoresis.

Subsequently, in step (c), genotyping of a target SSR marker is carried out based on the distribution of determined molecular weights of DNA fragments. The thus determined genotype is optionally compared with the genotype of a relevant SSR marker of a known variety/line which has previously been known or has been obtained as above, to determine what kind of variety/line the determined genotype belongs to, or to determine whether the determined genotype corresponds to none of known varieties/lines, or to determine the degree of affinity with a known specific variety/line.

The method of the present invention is advantageous in that a wider range of varieties/lines can be identified and reproducibility is higher, compared with, for example, sugarcane SSR markers disclosed in Non-Patent Document 1, based on the number of characteristic DNA sequences that can be used and SSR diversity in the sequences.

Further, the present invention encompasses a kit for carrying out the method of the present invention. The kit of the present invention comprises at least one primer set consisting of a forward and reverse primers that specifically amplify an SSR marker in the above characteristic DNA sequence.

The lengths of a forward primer and a reverse primer comprised in the kit of the present invention are not particularly limited as long as a target region can specifically be amplified. For instance, such length can fall within the range of 15 to 50 nucleotides and preferably 17 to 25 nucleotides.

Examples of such primer set are provided in table 5 shown below.

The primer set comprised in the kit of the present invention is preferably labeled at 5'-end for the convenience of subsequent determination of the molecular weights of amplified DNA fragments. Labeling can be carried out by a means known to persons skilled in the art, including, but are not limited to, FITC, $^{32}$P, alkaline phosphatase, rhodamine, fluorescamine, dansyl, and derivatives thereof.

Preferably, the kit of the present invention further comprises a correspondence table regarding the genotype of an SSR marker(s) in the above characteristic DNA sequence(s), obtained from known sugarcane varieties/lines. Based on the genotyping results obtained from a plant of the genus *Saccharum* to be tested with the use of the kit, it can be readily determined what kind of variety/line the plant of the genus *Saccharum* to be tested belongs to, or whether the plant of the genus *Saccharum* to be tested belongs to no known varieties/lines, or the degree of affinity with a known specific variety/line.

The present invention is hereafter described in greater detail with reference to the following examples, although the technical scope of the present invention is not limited thereto.

EXAMPLES

Example 1

Primary Selection of SSR Markers for Variety/Line Identification

The degree of amplification of an SSR region in an SSR marker was evaluated with the use of 96 lines of the genus *Saccharum*. As a result of PCR reaction and capillary electrophoresis, amplified fragments (bands) of the SSR region were confirmed for all examined SSR markers. Clear band patterns were obtained from 14 SSR markers among the same. However, unclear band patterns were obtained from 4 SSR markers (STY050, STY126, STY149, and STY167) (FIG. 1, table 1). The presence of unclear band patterns makes it difficult to analyze a plurality of samples. Therefore, 14 SSR markers, excluding 4 such SSR markers, were selected by primary selection.

TABLE 1

SSR markers examined for development of line identification technology and primary selection results

| SSR marker | Band pattern | Primary selection |
|---|---|---|
| STY050 | Unclear | x |
| STY099 | Clear | o |
| STY117 | Clear | o |
| STY120 | Clear | o |
| STY123 | Clear | o |
| STY126 | Unclear | x |
| STY127 | Clear | o |
| STY133 | Clear | o |
| STY137 | Clear | o |
| STY144 | Clear | o |
| STY145 | Clear | o |

TABLE 1-continued

SSR markers examined for development of line identification technology and primary selection results

| SSR marker | Band pattern | Primary selection |
|---|---|---|
| STY149 | Unclear | x |
| STY162 | Clear | o |
| STY166 | Clear | o |
| STY167 | Unclear | x |
| STY168 | Clear | o |
| STY173 | Clear | o |
| STY200 | Clear | o |

Example 2

Stability Test of SSR Markers for Variety/Line Identification

Figure 2:
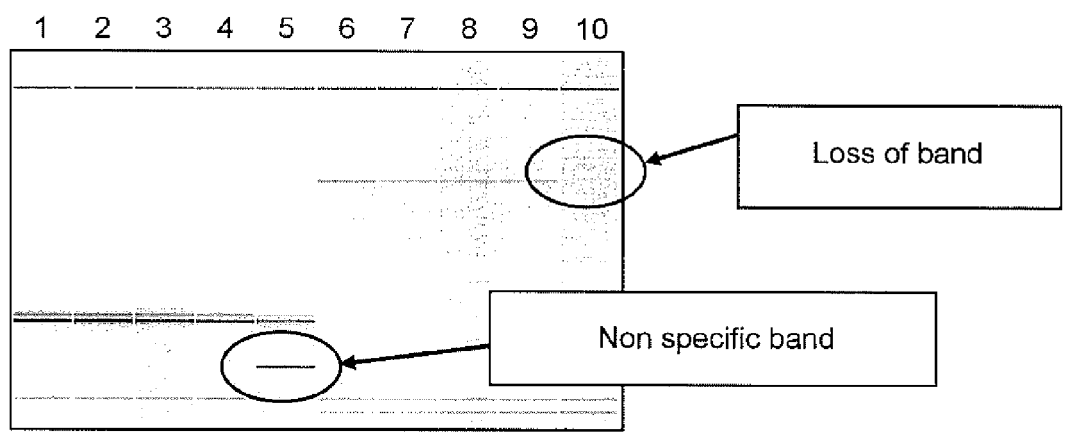
FIG. 2 shows changes in the electrophoresis image for SSR markers STY120 and STY162 due to different DNA contents: lanes 1 to 5: SSR marker STY120 (DNA contents: 3-fold, 2-fold, standard (24 ng), ½, and ⅓ from the left); and lanes 6 to 10: SSR marker STY162 (DNA contents: 3-fold, 2-fold, standard (24 ng), ½, and ⅓ from the left).

With the use of B3439 DNA, 14 SSR markers selected by primary selection were evaluated in terms of stability in response to changes in the DNA content upon PCR reaction. As a result, in the case of a PCR reaction at a DNA content of 12 ng (half amount of that used for a general PCR reaction) or more, changes in the band pattern in response to changes in the DNA content were not observed for any examined SSR marker. However, in the case of a PCR reaction at a DNA content of 8 ng (one-third amount of that used for a general PCR reaction), loss of band was found in 2 SSR markers, compared with the band patterns obtained at a DNA content of 12 ng (half amount of that used for a general PCR reaction) or more (FIG. 2, table 2).

The 2 above SSR markers were assumed to have low stability in response to changes in the DNA content. In line identification analysis, errors in terms of the DNA content are more likely to be caused in samples than by an apparatus, reagent, or the like. Therefore, it was thought to be difficult to use these 2 SSR markers for line identification. Based on the above results, 12 SSR markers having excellent stability in response to changes in the DNA content were selected for an SSR marker set for line identification. Meanwhile, at a decreased DNA content, an SSR marker generating a band below 60 bp was observed (FIG. 2). The SSR markers used herein were designed for amplification of 60-bp regions or larger regions. Therefore, it was thought that such a band below 60 bp had not been derived from an SSR region amplification fragment, and thus that it was a non-specific band.

TABLE 2

SSR marker amplification results based on the genomic DNA content

| SSR marker | DNA content (standard: 24 ng)* | | | | |
|---|---|---|---|---|---|
| | 3-fold | 2-fold | Standard | ½ | ⅓ |
| STY099 | O | O | O | O | O |
| STY117 | O | O | O | O | O |
| STY120 | O | O | O | O | O |
| STY123 | O | O | O | O | O |
| STY127 | O | O | O | O | X |
| STY133 | O | O | O | O | O |
| STY137 | O | O | O | O | O |
| STY144 | O | O | O | O | O |
| STY145 | O | O | O | O | O |
| STY162 | O | O | O | O | X |
| STY166 | O | O | O | O | O |
| STY168 | O | O | O | O | O |
| STY173 | O | O | O | O | O |
| STY200 | O | O | O | O | O |

*"X": Loss of band

Example 3

Identification Ability of SSR Markers for Variety/Line Identification

Figures 1, 3:
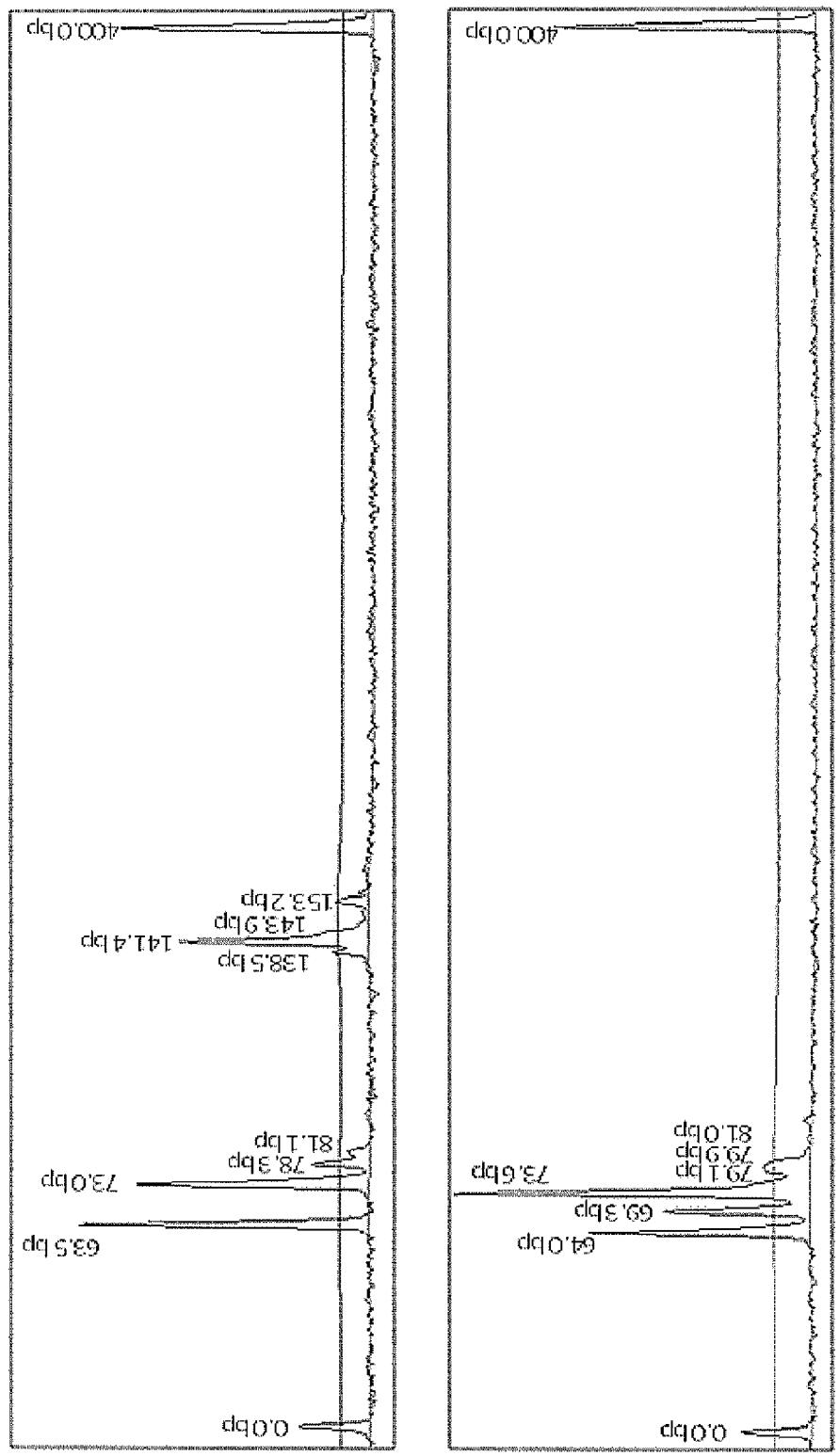
Figures 2, 3:
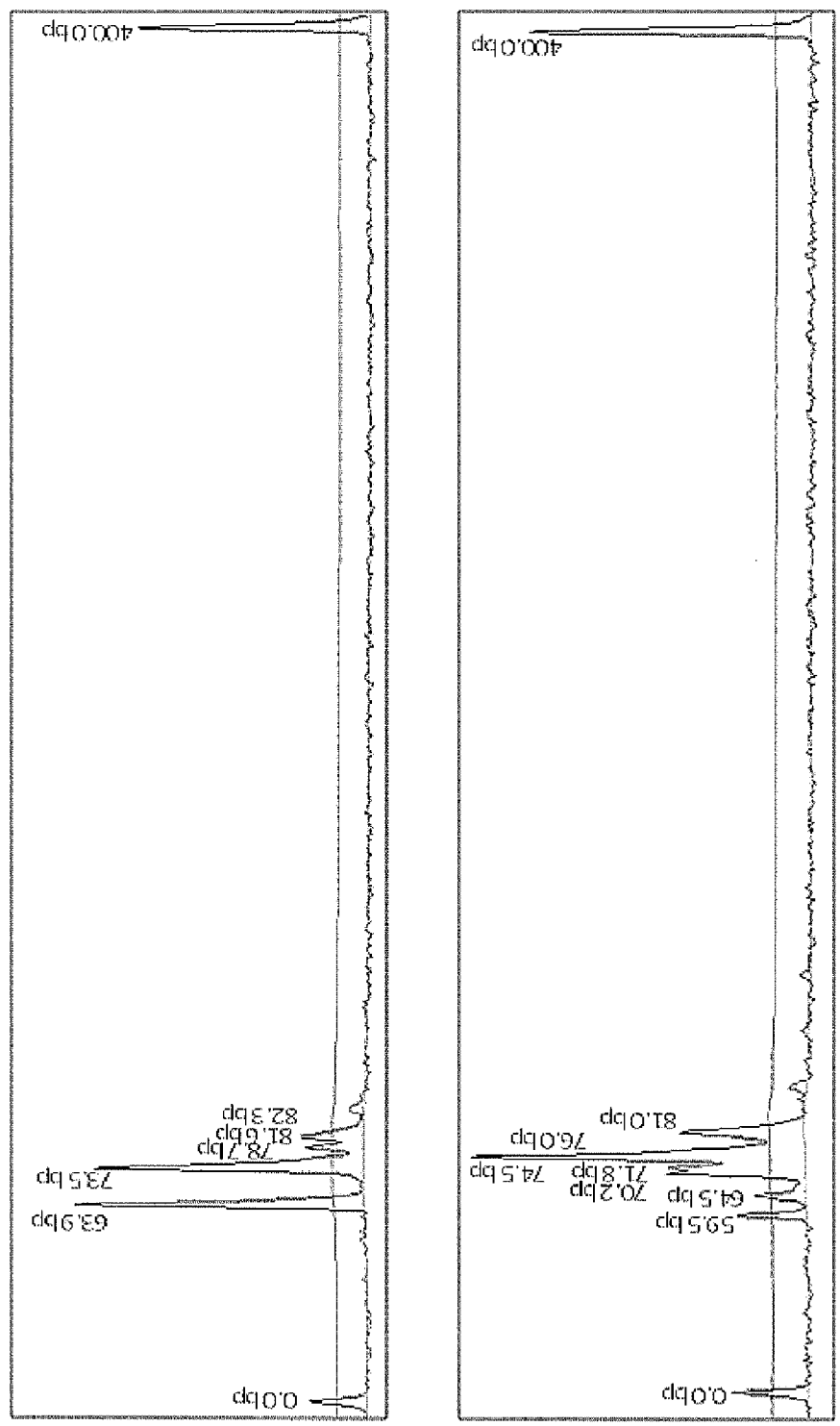

In order to evaluate the identification ability of an SSR marker STY133 for variety/line identification, 4 lines (NiF8, Ni9, NCO310, and F177) were examined in terms of band differences. The numbers of obtained bands were 43 bands, 35 bands, 39 bands, and 45 bands, respectively. The average number of common bands was 27.2 for all lines. Meanwhile, the average number of non-common bands was 26.7. Accordingly, the individual lines could be separately identified (FIG. 3).

Figure 4:
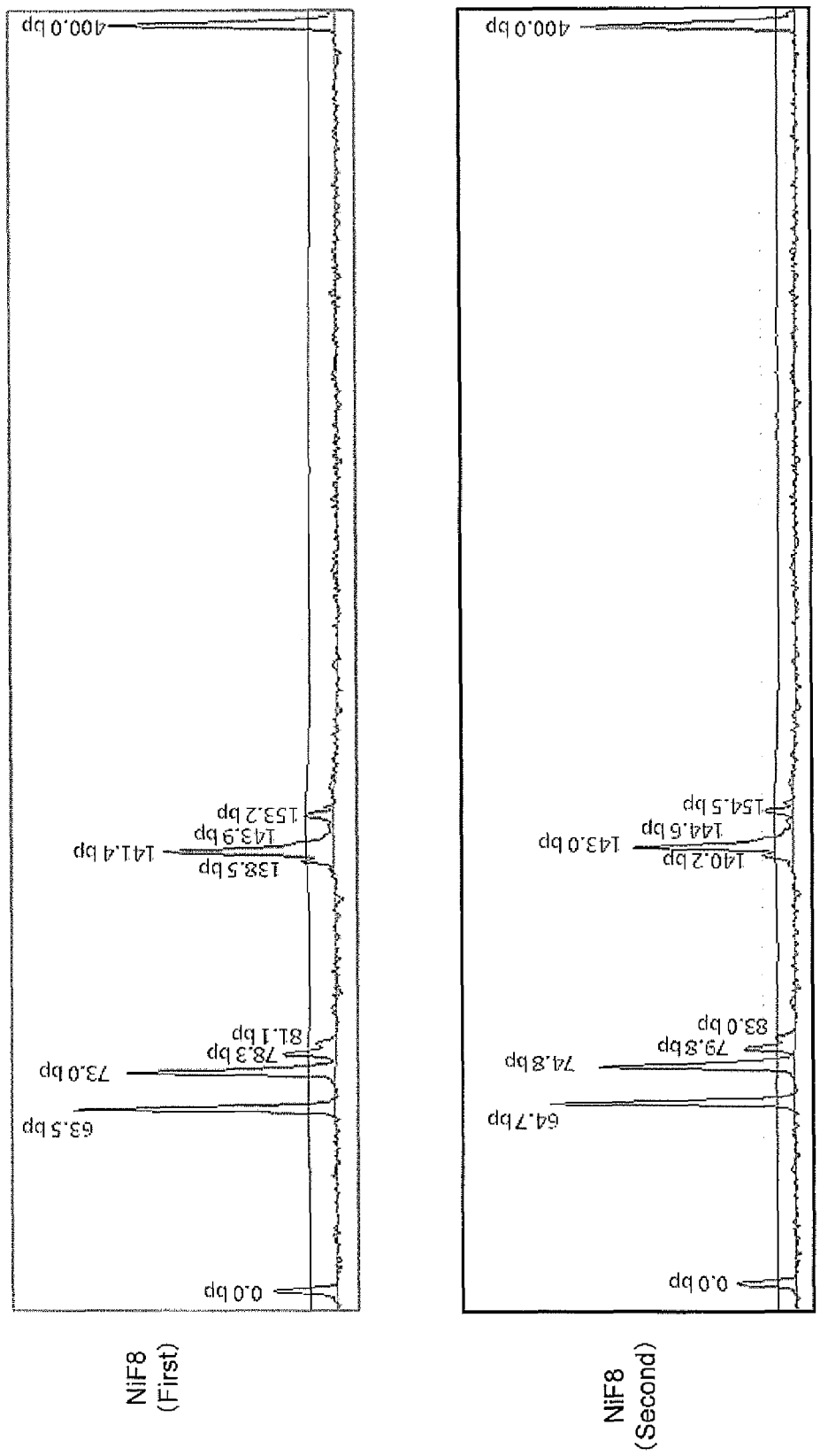
FIG. 4 shows partial charts indicating the reproducibility of polymorphism detection with the use of an SSR marker STY133.

In addition, as a result of evaluation of reproducibility of the STY133 band with the use of 4 lines (NiF8, Ni14, F160, and NCO310), reproducibility was confirmed for each line (FIG. 4).

Further, based on the results of the numbers of bands and the appearance rates for 125 lines of the genus *Saccharum*, the SSR marker set for line identification was evaluated in terms of the identification ability. As a result of analysis, the maximum, minimum, and average numbers of bands per SSR marker were 51, 15, and 29, respectively. In total, 348 bands were obtained (table 3). The maximum, minimum, and average appearance rates of the individual bands were 96.9%, 1.0%, and 10.8%, respectively. The maximum, minimum, and average numbers of bands for each line detected with an SSR marker set were 52, 24, and 39, respectively. The probability of accidental coincidence of all bands for two lines, which was obtained from the appearance rates of the individual bands and the number of bands for each line, was found to be very low (6.0E-6 or less).

TABLE 3

Number of polymorphisms in SSR markers

| SSR marker | Number of polymorphisms |
|---|---|
| STY099 | 27 |
| STY117 | 51 |
| STY120 | 27 |
| STY123 | 15 |
| STY127 | No data |
| STY133 | 36 |
| STY137 | 27 |
| STY144 | 25 |
| STY145 | 18 |
| STY162 | No data |
| STY166 | 15 |
| STY168 | 50 |
| STY173 | 15 |
| STY200 | 42 |
| | Total 348 |
| | Average 29 |

Example 4

For 125 varieties/lines of the genus *Saccharum*, the genotype of each SSR marker was determined with the use of SSR markers for variety/line identification.

Table 4 shown below lists genotyping results for each SSR marker obtained from 125 varieties/lines of plants of the genus *Saccharum* examined in this Example.

TABLE 4

SSR marker band patterns of sugarcane main varieties/lines

| Variety/Line name | STY099 | STY117 | STY120 | STY123 | STY133 | STY137 | STY144 | STY145 | STY166 | STY168 | STY173 | STY200 |
|---|---|---|---|---|---|---|---|---|---|---|---|---|
| Ni1 | A001 | B001 | C001 | D002 | E096 | F001 | G001 | H001 | I001 | J001 | K020 | L001 |
| NiN2 | A002 | B002 | C002 | D007 | E001 | F002 | G002 | H002 | I001 | J002 | K001 | L002 |
| NiF3 | A003 | B003 | C002 | D002 | E002 | F003 | G003 | H002 | I001 | J003 | K020 | L003 |
| NiF4 | A004 | B004 | C002 | D004 | E003 | F002 | G004 | H003 | I001 | J004 | K001 | L004 |
| NiF5 | A005 | B002 | C003 | D001 | E004 | F004 | G003 | H001 | I002 | J004 | K020 | L005 |
| Ni6 | A006 | B005 | C004 | D001 | E005 | F005 | G002 | H004 | I002 | J005 | K001 | L006 |
| NiN7 | A007 | B002 | C005 | D007 | E006 | F006 | G005 | H001 | I002 | J005 | K001 | L007 |
| NiF8 | A008 | B002 | C006 | D007 | E007 | F007 | G006 | H001 | I001 | J006 | K001 | L008 |
| Ni9 | A009 | B004 | C002 | D004 | E008 | F002 | G004 | H003 | I001 | J004 | K001 | L009 |
| NiTn10 | A010 | B006 | C007 | D015 | E009 | F008 | G004 | H003 | I001 | J004 | K001 | L010 |
| Ni11 | A011 | B074 | C008 | D007 | E010 | F009 | G007 | H001 | I001 | J007 | K002 | L011 |
| Ni12 | A012 | B007 | C009 | D002 | E011 | F010 | G007 | H004 | I001 | J008 | K020 | L012 |
| Ni14 | A013 | B008 | C010 | D015 | E010 | F011 | G008 | H005 | I001 | J005 | K001 | L013 |
| Ni15 | A014 | B009 | C011 | D015 | E012 | F002 | G009 | H006 | I001 | J004 | K020 | L014 |
| Ni16 | A015 | B010 | C012 | D003 | E013 | F012 | G008 | H001 | I002 | J005 | K020 | L015 |
| Ni17 | A016 | B002 | C011 | D007 | E014 | F006 | G010 | H005 | I001 | J004 | K001 | L016 |
| NiTn19 | A017 | B011 | C013 | D002 | E015 | F013 | G007 | H001 | I002 | J009 | K002 | L017 |
| NiTn20 | A018 | B012 | C013 | D002 | E016 | F014 | G007 | H002 | I002 | J010 | K020 | L018 |
| Ni22 | A019 | B002 | C014 | D004 | E017 | F009 | G004 | H003 | I001 | J006 | K020 | L019 |
| Ni23 | A019 | B006 | C014 | D004 | E007 | F002 | G004 | H001 | I001 | J005 | K001 | L020 |
| F135 | A020 | B013 | C002 | D007 | E018 | F002 | G011 | H001 | I002 | J002 | K020 | L021 |
| F141 | A021 | B014 | C014 | D007 | E019 | F015 | G008 | H004 | I001 | J005 | K020 | L022 |
| F146 | A022 | B002 | C015 | D007 | E020 | F016 | G008 | H007 | I003 | J003 | K020 | L023 |
| F149A | A023 | B015 | C014 | D007 | E021 | F017 | G007 | H001 | I001 | J011 | K020 | L024 |
| F160 | A024 | B002 | C014 | D007 | E010 | F003 | G002 | H002 | I001 | J005 | K001 | L025 |
| F172 | A025 | B002 | C013 | D002 | E022 | F019 | G008 | H004 | I002 | J010 | K002 | L026 |
| F175 | A026 | B002 | C002 | D004 | E023 | F020 | G007 | H005 | I001 | J012 | K020 | L027 |
| F177 | A027 | B016 | C016 | D004 | E024 | F012 | G007 | H001 | I002 | J004 | K002 | L028 |
| Nco310 | A028 | B002 | C002 | D015 | E025 | F021 | G003 | H005 | I002 | J004 | K001 | L009 |
| NCo310xSorghumSart | A029 | B017 | C017 | D005 | E026 | F022 | G012 | H004 | I001 | J002 | K003 | L029 |
| NCo376 | A030 | B002 | C002 | D007 | E027 | F002 | G011 | H001 | I002 | J002 | K020 | L030 |
| P0J2725 | A031 | B018 | C018 | D004 | E028 | F023 | G013 | H004 | I004 | J013 | K004 | L031 |
| P0J0143 | A028 | B017 | C019 | D010 | E029 | F024 | G005 | H005 | I002 | J014 | K002 | L032 |
| P0J2878 | A032 | B019 | C020 | D015 | E030 | F025 | G009 | H008 | I001 | J015 | K020 | L033 |
| Badila | A033 | B020 | C002 | D015 | E031 | F026 | G008 | H004 | I002 | J004 | K001 | L034 |
| Chittan | A034 | B021 | C021 | D007 | E019 | F006 | G008 | H004 | I005 | J016 | K005 | L035 |
| GlagahKloet | A035 | B022 | C022 | D021 | E032 | F027 | G014 | H009 | I006 | J017 | K020 | L036 |
| robustum5 | A036 | B023 | C023 | D006 | E033 | F028 | G015 | H005 | I002 | J010 | K006 | L037 |
| IJ-76-349 | A037 | B002 | C006 | D007 | E034 | F029 | G003 | H001 | I001 | J006 | K001 | L008 |
| Q117 | A038 | B004 | C002 | D007 | E023 | F030 | G007 | H010 | I001 | J012 | K020 | L038 |
| Q124 | A039 | B024 | C024 | D005 | E035 | F031 | G016 | H011 | I002 | J004 | K001 | L039 |
| B3439 | A040 | B002 | C025 | D015 | E036 | F032 | G017 | H005 | I002 | J004 | K001 | L009 |
| CAC57-02 | A041 | B014 | C014 | D007 | E037 | F002 | G009 | H004 | I001 | J008 | K002 | L040 |
| CB40-77 | A042 | B025 | C026 | D002 | E038 | F033 | G018 | H004 | I001 | J004 | K020 | L041 |
| Co0290 | A043 | B017 | C027 | D002 | E039 | F034 | G019 | H001 | I005 | J004 | K002 | L042 |
| Co0312 | A044 | B017 | C028 | D007 | E040 | F035 | G020 | H012 | I007 | J004 | K020 | L043 |
| Co0331 | A012 | B002 | C029 | D002 | E041 | F009 | G018 | H004 | I001 | J005 | K020 | L044 |
| Co0356 | A045 | B024 | C030 | D002 | E042 | F036 | G008 | H001 | I001 | J018 | K020 | L045 |
| Co0421 | A046 | B026 | C078 | D015 | E043 | F009 | G018 | H004 | I001 | J019 | K020 | L046 |
| Co0453 | A047 | B024 | C031 | D015 | E043 | F009 | G018 | H004 | I001 | J019 | K020 | L047 |
| Co0740B | A048 | B002 | C032 | D007 | E044 | F037 | G021 | H001 | I002 | J020 | K001 | L024 |
| Co0798 | A033 | B002 | C033 | D007 | E045 | F038 | G005 | H004 | I002 | J002 | K007 | L048 |
| Co1001B | A028 | B023 | C002 | D012 | E046 | F002 | G008 | H004 | I002 | J003 | K020 | L049 |
| CP33-224 | A049 | B002 | C034 | D007 | E047 | F039 | G005 | H001 | I001 | J006 | K001 | L050 |
| CP34-079 | A050 | B027 | C003 | D007 | E048 | F040 | G008 | H012 | I001 | J004 | K002 | L051 |
| CP36-013 | A028 | B028 | C002 | D002 | E025 | F002 | G008 | H004 | I001 | J006 | K020 | L052 |
| CP36-211 | A028 | B026 | C035 | D010 | E029 | F041 | G022 | H005 | I002 | J002 | K002 | L053 |
| CP43-033 | A028 | B026 | C035 | D010 | E029 | F042 | G018 | H005 | I001 | J010 | K002 | L053 |
| CP44-101 | A028 | B017 | C035 | D010 | E029 | F043 | G018 | H005 | I001 | J002 | K002 | L053 |
| CP44-155 | A050 | B029 | C035 | D008 | E049 | F044 | G001 | H001 | I001 | J006 | K002 | L054 |
| CP45-150 | A028 | B017 | C035 | D010 | E029 | F041 | G018 | H005 | I001 | J010 | K002 | L053 |
| CP52-068D | A028 | B030 | C036 | D009 | E050 | F045 | G021 | H013 | I001 | J005 | K001 | L055 |
| CP57-614A | A051 | B028 | C027 | D007 | E051 | F046 | G008 | H001 | I001 | J006 | K020 | L002 |
| CP57-621 | A052 | B017 | C002 | D009 | E052 | F046 | G005 | H004 | I001 | J021 | K020 | L056 |
| CP77-0415 | A028 | B031 | C037 | D010 | E050 | F047 | G019 | H013 | I008 | J005 | K001 | L055 |
| H32-8560 | A053 | B026 | C038 | D002 | E053 | F048 | G023 | H004 | I001 | J022 | K002 | L057 |
| M202x46 | A054 | B032 | C039 | D011 | E054 | F049 | G009 | H004 | I001 | J004 | K008 | L058 |
| PT43-52 | A055 | B029 | C040 | D012 | E055 | F009 | G009 | H001 | I001 | J002 | K020 | L059 |
| Q068 | A056 | B002 | C041 | D007 | E056 | F009 | G008 | H001 | I001 | J023 | K020 | L060 |
| Q073 | A057 | B002 | C010 | D015 | E011 | F040 | G009 | H004 | I001 | J001 | K009 | L061 |
| Eros | A058 | B034 | C002 | D015 | E023 | F022 | G024 | H005 | I002 | J003 | K020 | L062 |
| R397 | A059 | B002 | C042 | D002 | E057 | F017 | G001 | H004 | I001 | J024 | K020 | L063 |
| Trojan | A060 | B002 | C001 | D013 | E058 | F040 | G009 | H004 | I001 | J025 | K020 | L064 |
| US72-1288 | A061 | B035 | C043 | D015 | E059 | F050 | G018 | H001 | I002 | J026 | K020 | L064 |
| US56-15-2 | A062 | B036 | C044 | D014 | E060 | F051 | G025 | H014 | I009 | J027 | K020 | L065 |
| US56-15-8 | A063 | B037 | C045 | D015 | E061 | F052 | G026 | H015 | I002 | J028 | K020 | L066 |

TABLE 4-continued

SSR marker band patterns of sugarcane main varieties/lines

| Variety/Line name | STY099 | STY117 | STY120 | STY123 | STY133 | STY137 | STY144 | STY145 | STY166 | STY168 | STY173 | STY200 |
|---|---|---|---|---|---|---|---|---|---|---|---|---|
| SES182 | A064 | B038 | C046 | D021 | E062 | F002 | G027 | H016 | I005 | J029 | K020 | L067 |
| SES205A | A065 | B039 | C047 | D021 | E063 | F039 | G028 | H017 | I005 | J030 | K020 | L068 |
| SES231 | A066 | B040 | C048 | D021 | E064 | F053 | G029 | H018 | I010 | J031 | K020 | L069 |
| IJ76-514 | A067 | B017 | C078 | D015 | E065 | F002 | G026 | H004 | I001 | J032 | K020 | L070 |
| IN84-111 | A068 | B041 | C049 | D021 | E066 | F054 | G029 | H017 | I011 | J033 | K020 | L071 |
| IS76-174 | A069 | B042 | C050 | D021 | E067 | F055 | G030 | H019 | I011 | J034 | K020 | L072 |
| JW19 | A069 | B043 | C051 | D021 | E068 | F055 | G030 | H019 | I011 | J034 | K020 | L072 |
| JW28 | A070 | B044 | C052 | D016 | E069 | F056 | G029 | H001 | I012 | J035 | K020 | L073 |
| JW49 | A071 | B045 | C053 | D004 | E070 | F057 | G031 | H001 | I011 | J036 | K020 | L074 |
| JW50 | A072 | B046 | C054 | D016 | E071 | F058 | G042 | H020 | I012 | J035 | K020 | L073 |
| JW69 | A073 | B047 | C055 | D021 | E072 | F059 | G025 | H021 | I011 | J037 | K020 | L075 |
| JW97 | A074 | B048 | C056 | D021 | E073 | F060 | G032 | H022 | I011 | J038 | K020 | L076 |
| JW111 | A074 | B049 | C056 | D016 | E073 | F060 | G032 | H022 | I011 | J039 | K020 | L076 |
| JW233 | A075 | B050 | C057 | D021 | E074 | F006 | G029 | H023 | I012 | J040 | K020 | L020 |
| JW516 | A076 | B051 | C058 | D021 | E075 | F060 | G033 | H022 | I013 | J041 | K020 | L077 |
| JW544 | A077 | B052 | C059 | D016 | E071 | F061 | G042 | H001 | I012 | J035 | K020 | L078 |
| 06JW-1 | A078 | B044 | C060 | D016 | E074 | F062 | G042 | H001 | I006 | J042 | K020 | L073 |
| Yomitanzan | A079 | B053 | C061 | D004 | E076 | F063 | G008 | H010 | I002 | J043 | K010 | L079 |
| Maneria | A079 | B054 | C061 | D004 | E076 | F063 | G008 | H010 | I002 | J043 | K011 | L079 |
| Chunee | A080 | B055 | C062 | D021 | E076 | F064 | G008 | H002 | I002 | J044 | K012 | L080 |
| KRF093-1 | A081 | B056 | C063 | D004 | E077 | F065 | G042 | H001 | I002 | J012 | K001 | L081 |
| Burma | A082 | B057 | C064 | D004 | E078 | F021 | G008 | H024 | I014 | J045 | K013 | L082 |
| S. spont. Glagah | A083 | B058 | C065 | D021 | E079 | F066 | G042 | H025 | I010 | J046 | K020 | L083 |
| PonapeW. T | A083 | B059 | C066 | D021 | E079 | F067 | G042 | H025 | I010 | J046 | K020 | L084 |
| Tainan | A084 | B060 | C067 | D021 | E080 | F068 | G029 | H026 | I015 | J059 | K020 | L085 |
| PonapeW. S | A085 | B002 | C005 | D007 | E081 | F016 | G034 | H001 | I001 | J032 | K014 | L086 |
| Marga | A086 | B074 | C068 | D021 | E082 | F069 | G042 | H027 | I012 | J029 | K015 | L087 |
| Pana | A087 | B061 | C069 | D021 | E083 | F070 | G035 | H028 | I011 | J047 | K020 | L088 |
| Cavengerie | A056 | B013 | C027 | D015 | E035 | F006 | G008 | H001 | I001 | J002 | K001 | L089 |
| RoseBamboo | A088 | B062 | C070 | D019 | E084 | F071 | G036 | H001 | I001 | J048 | K016 | L100 |
| BoisRouge | A089 | B063 | C016 | D010 | E085 | F072 | G037 | H004 | I016 | J049 | K011 | L100 |
| BambooCane | A090 | B064 | C071 | D017 | E086 | F073 | G008 | H029 | I002 | J050 | K011 | L090 |
| BlackTanna | A091 | B024 | C016 | D018 | E087 | F006 | G034 | H001 | I002 | J006 | K001 | L091 |
| Wakayama | A092 | B065 | C071 | D004 | E088 | F073 | G008 | H029 | I001 | J050 | K011 | L092 |
| NatalUba | A093 | B066 | C071 | D004 | E088 | F073 | G008 | H029 | I001 | J050 | K011 | L093 |
| Tekcha | A094 | B067 | C072 | D004 | E088 | F074 | G038 | H029 | I001 | J051 | K017 | L092 |
| Kouchi | A002 | B002 | C016 | D015 | E089 | F075 | G008 | H001 | I001 | J002 | K014 | L094 |
| Mungo254 | A095 | B068 | C016 | D019 | E090 | F076 | G036 | H001 | I001 | J052 | K010 | L100 |
| Nargori | A096 | B069 | C016 | D019 | E090 | F076 | G036 | H001 | I001 | J052 | K003 | L100 |
| PonapeHuruki-mura | A083 | B070 | C073 | D021 | E079 | F077 | G042 | H030 | I017 | J053 | K020 | L095 |
| Molokai1032 | A097 | B071 | C074 | D021 | E091 | F078 | G039 | H031 | I012 | J054 | K020 | L024 |
| Robustum6 | A098 | B072 | C001 | D020 | E092 | F079 | G040 | H004 | I002 | J055 | K018 | L096 |
| Robustum9 | A099 | B073 | C075 | D021 | E093 | F011 | G008 | H001 | I018 | J056 | K020 | L097 |
| Robustum16 | A100 | B002 | C076 | D021 | E093 | F011 | G020 | H001 | I002 | J056 | K020 | L098 |
| Robustum21 | A101 | B054 | C077 | D007 | E094 | F080 | G041 | H032 | I002 | J057 | K019 | L099 |
| IK76-126 | A102 | B074 | C078 | D021 | E096 | F002 | G042 | H033 | I019 | J034 | K020 | L100 |
| JW630 | A102 | B074 | C078 | D021 | E096 | F081 | G042 | H033 | I019 | J058 | K020 | L100 |
| IS76-156 | A102 | B074 | C078 | D021 | E096 | F082 | G042 | H033 | I019 | J034 | K020 | L100 |
| R570 | A103 | B074 | C078 | D021 | E095 | F083 | G008 | H004 | I019 | J059 | K020 | L100 |

In the table, the individual SSR markers are represented by letters "A" to "L," with numbers representing the allelic genotypes thereof. For instance, "STY099" indicates the presence of 103 types of genotypes among 125 tested varieties/lines.

As is apparent from table 4, all 125 tested sugarcane varieties/lines could be identified using the above SSR markers, if necessary, in combination.

Table 5 shown below lists PCR primer sequences for SSR marker amplification used in the above Examples.

TABLE 5

SSR marker primer sequence

| SSR marker name | Primer sequence Forward | Reverse |
|---|---|---|
| STY099 | CCTGAATCCTCTCCCATCCT (SEQ ID NO: 15) | GAAGGGTTTTGTGTAGGCCA (SEQ ID NO: 16) |
| STY117 | GGTGCTGGCTTTATGACGTT (SEQ ID NO: 17) | TGCTTGGGACAAAAGGCTAT (SEQ ID NO: 18) |

TABLE 5-continued

SSR marker primer sequence

| SSR marker name | Primer sequence Forward | Reverse |
|---|---|---|
| STY120 | CCTAGCAACATAAGAGGGCTT (SEQ ID NO: 19) | CCAACATGAACACAACGGAG (SEQ ID NO: 20) |
| STY123 | TTGACCAAAGTGCCATCTGT (SEQ ID NO: 21) | TGTAGCCTACCCCAACTTGC (SEQ ID NO: 22) |
| STY127 | TCCGGACAAGGTTTATGAGTTT (SEQ ID NO: 23) | GGGCTCTGGCTAGGAAAGAA (SEQ ID NO: 24) |
| STY133 | GCGTGAAGTTGATGCTGGTA (SEQ ID NO: 25) | GCCGTAGGTTGGTCAAAAGA (SEQ ID NO: 26) |
| STY137 | CTGCCATCATCCCCTTCTTA (SEQ ID NO: 27) | AGCAGGCTAAAAACAGACTGG (SEQ ID NO: 28) |
| STY144 | TGCTTGGGACAAAAGGCTAT (SEQ ID NO: 29) | TGGACCAAAACGTCAGGAAT (SEQ ID NO: 30) |
| STY145 | CCAACCCCTCATCTTCAGAC (SEQ ID NO: 31) | GACGAGGATGAGGAGGAACA (SEQ ID NO: 32) |
| STY162 | GGGAAACAATTTCCGTCAGA (SEQ ID NO: 33) | TGCTTGGGACAAAAGGCTAT (SEQ ID NO: 34) |
| STY166 | CTATAAAAGGGGAGGCAGGG (SEQ ID NO: 35) | CCAGGTCTCTTCAGGGGATT (SEQ ID NO: 36) |
| STY168 | CCCGACTAACCTGTGCTGTT (SEQ ID NO: 37) | CATGGGATGGGATCAGATGT (SEQ ID NO: 38) |
| STY173 | CATCATTGGACGCTGTTACC (SEQ ID NO: 39) | CAAGACTGGAACTGCAAGAAA (SEQ ID NO: 40) |
| STY200 | CAAGCCTACTCCCATACTCCA (SEQ ID NO: 41) | TGTCCCAACTAGGGAAGGAA (SEQ ID NO: 42) |

INDUSTRIAL APPLICABILITY

According to the method and the kit of the present invention, a wide range of varieties/lines of plants of the genus *Saccharum* can easily be identified with high accuracy and high reproducibility.

In view of the above, it is expected that industrial advantages described below, for example, can be obtained.

(1) It is possible to confirm the original line/variety of a plant of the genus *Saccharum* and the occurrence or nonoccurrence of outcrossing or mixing up of varieties/lines during production or within the marketing or distribution chain.

(2) Plants of the genus *Saccharum* having excellent characteristics can be clearly identified, and thus improvement of next-generation energy crops can be significantly promoted.

(3) The development of varieties having excellent heterosis can be promoted.

(4) Degrees of affinity among varieties/lines of the genus *Saccharum* can be obtained, and thus affinity-related information can be provided.

The invention claimed is:

1. A method for identifying the variety/line of a plant of the genus *Saccharum*, comprising a step of genotyping at least one simple sequence repeat selected from simple sequence repeat polymorphisms in DNA sequences of SEQ ID NOs: 1, 2, 3, 5, 6, 10, and 12, wherein the step of genotyping is carried out by the steps of:
   (a) carrying out PCR amplification using DNA extracted from a sugarcane to be identified as a template and a primer set consisting of a forward and a reverse primer that specifically amplify a region containing a simple sequence repeat in a DNA sequence of SEQ ID NOs: 1, 2, 3, 5, 6, 10, or 12;
   (b) determining the molecular weights of amplified DNA fragments; and
   (c) performing genotyping of the region containing a simple sequence repeat based on distribution of molecular weights.

2. The method according to claim 1, further comprising a step of genotyping simple sequence repeat polymorphisms in the DNA sequence(s) represented by SEQ ID NO(S): 13 and/or 14.

3. The method according to claim 1, wherein the determination of the molecular weights of the amplified DNA fragments in step (b) is performed by capillary electrophoresis.

4. The method according to claim 1, further comprising comparing the genotype determined with that obtained from a known sugarcane variety/line in step (c).

* * * * *